US006685787B2

(12) United States Patent
Linares et al.

(10) Patent No.: US 6,685,787 B2
(45) Date of Patent: Feb. 3, 2004

(54) METHOD OF MAKING APPLICATORS HAVING IMPROVED FINGER GRIP FEATURES

(75) Inventors: Carlos G. Linares, Mountainside, NJ (US); Linda M. Pierson, Somerville, NJ (US)

(73) Assignee: McNeil-PPC, Inc., Skillman, NY (US)

( * ) Notice: Subject to any disclaimer, the term of this patent is extended or adjusted under 35 U.S.C. 154(b) by 244 days.

(21) Appl. No.: 10/035,399

(22) Filed: Nov. 9, 2001

(65) Prior Publication Data

US 2002/0056504 A1 May 16, 2002

Related U.S. Application Data

(62) Division of application No. 09/340,312, filed on Jun. 25, 1999, now Pat. No. 6,368,442.

(51) Int. Cl.⁷ .................................................. A61F 13/20
(52) U.S. Cl. ...................... 156/198; 156/203; 156/215; 156/218; 156/259
(58) Field of Search .................................. 156/203, 212, 156/218, 259, 267, 215, 198; 604/11–18

(56) References Cited

U.S. PATENT DOCUMENTS

| | | |
|---|---|---|
| 2,751,907 A | 6/1956 | Hickey |
| 3,086,527 A | 4/1963 | Forrest |
| 3,757,781 A | 9/1973 | Smart |
| 3,831,605 A | 8/1974 | Fournier |
| 3,921,632 A | 11/1975 | Bardani |
| 4,060,083 A | 11/1977 | Hanson |
| 4,361,150 A | 11/1982 | Voss |
| 4,428,370 A | 1/1984 | Keely |
| 4,447,222 A | 5/1984 | Sartinoranont |
| 4,508,531 A | 4/1985 | Whitehead |
| 4,536,178 A | 8/1985 | Lichstein et al. |
| 4,573,963 A | 3/1986 | Sheldon |
| 4,573,964 A | 3/1986 | Huffman |
| 4,755,164 A | 7/1988 | Hinzmann |
| 4,822,332 A | 4/1989 | Kajander |
| 4,900,299 A | 2/1990 | Webb |
| 4,921,474 A | 5/1990 | Suzuki et al. |
| 5,002,526 A | 3/1991 | Herring |
| 5,158,535 A | 10/1992 | Paul et al. |
| 5,330,421 A | 7/1994 | Tarr et al. |
| 5,346,468 A | 9/1994 | Campion et al. |
| 5,348,534 A | 9/1994 | Tomaszewski et al. |
| 5,350,354 A | 9/1994 | Billmers |
| 5,709,652 A | 1/1998 | Hagerty |
| 5,782,793 A | 7/1998 | Nielsen et al. |
| 5,782,794 A | 7/1998 | Assenheimer Downs |
| 5,788,663 A | 8/1998 | Igaue et al. |
| 5,800,377 A | 9/1998 | Campion et al. |
| 5,823,988 A | 10/1998 | Orenga et al. |
| 5,827,214 A | 10/1998 | Fox et al. |
| 6,171,426 B1 | 1/2001 | Blanchard |
| 6,264,626 B1 | 7/2001 | Linares et al. |

FOREIGN PATENT DOCUMENTS

| | | |
|---|---|---|
| EP | 0418791 A | 3/1991 |
| EP | 0966941 A2 | 12/1999 |
| GB | 2166656 A | 5/1986 |

OTHER PUBLICATIONS

McNeil–PPC, Inc. PCT/US00/12165 Search Report.
McNeil–PPC, Inc. PCT/US00/12169 Search Report.

Primary Examiner—Sam Chuan Yao

(57) ABSTRACT

The present invention relates to methods of making applicators for inserting materials into body cavities. The applicators comprise a tubular insertion member having an insertion end and a gripper end opposite thereof. The gripper end has an indentation with a shoulder on each end of the indentation. The shoulder most proximal the insertion end provides resistance to finger slip during the step of inserting the applicator into a body cavity. Whereas the shoulder most proximal the gripper end provides resistance to finger slip during the step of expelling material substantially contained by the applicator. The shoulder most proximal the gripper end also provides secure handling of the applicator while removing the applicator from the body after the expulsion step has been completed.

7 Claims, 3 Drawing Sheets

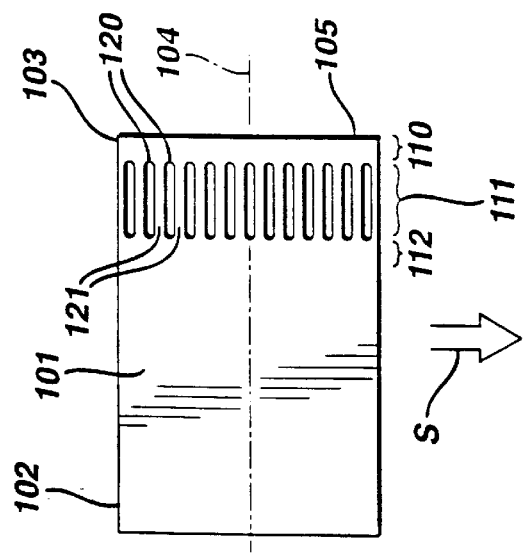
FIG. 2A
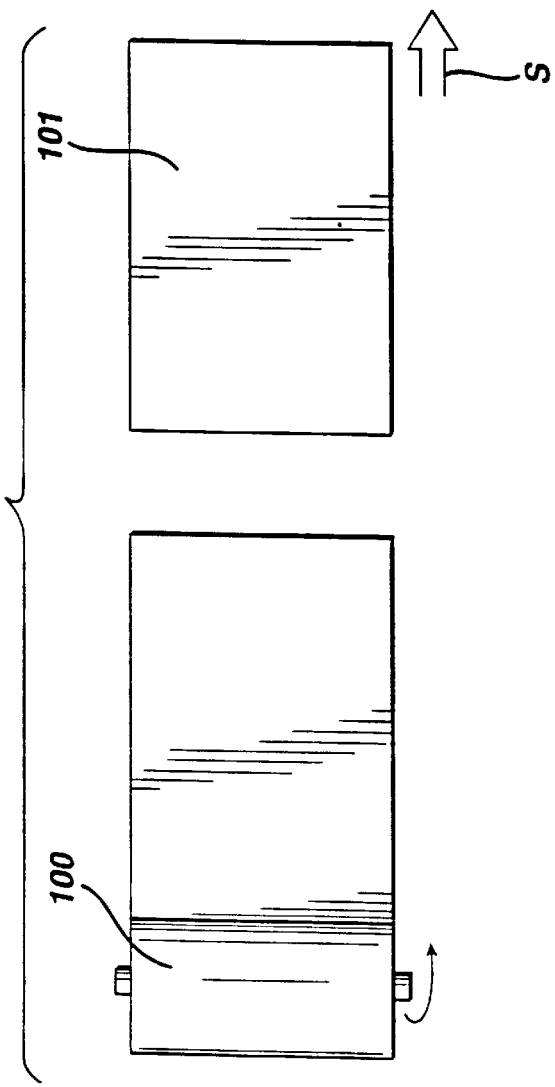
FIG. 2B
FIG. 2C
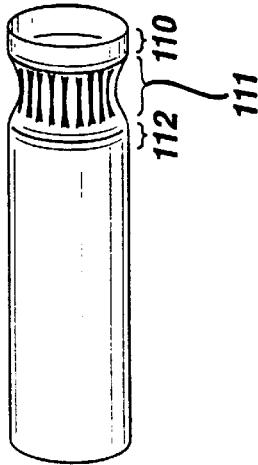
FIG. 2D

METHOD OF MAKING APPLICATORS HAVING IMPROVED FINGER GRIP FEATURES

CROSS-REFERENCE TO RELATED APPLICATIONS

This is a division of prior application Ser. No. 09/340,312 filed Jun. 25, 1999, now U.S. Pat. No. 6,368,442, the contents of which are herein incorporated by reference.

FIELD OF THE INVENTION

The present invention relates to a process of making applicators for delivering materials into mammalian body cavities having an indentation in a finger grip region with shoulders on each end of the indentation. The applicator is particularly useful for delivering catamenial devices into a vaginal canal.

BACKGROUND OF THE INVENTION

Applicators for delivering materials into a body cavity typically comprise a tubular insertion member having an insertion end and a gripper end opposite thereof, and an elongate expulsion member slideably fitted within the tubular insertion member for expelling the contained materials. The gripper end will generally incorporate features to allow a user to more or less securely hold the applicator during use—inserting the applicator into a body cavity, expelling a substantially enclosed material contained by the applicator, and withdrawing the applicator from the body.

Attempts have been made to improve the user's ability to manipulate the applicator during use. One approach is to significantly reduce the diameter of the applicator in the gripper end, as can be seen in Whitehead, U.S. Pat. No. 4,508,531. Whitehead discloses providing a blank with a plurality of slightly recessed areas outlined by scored lines, which result in a reduced diameter gripping portion when the blank is formed into a tubular structure.

Similar examples can be seen in Huffman, U.S. Pat. No. 4,573,964, and Sheldon, U.S. Pat. No. 4,573,963. Huffman and Sheldon disclose providing a finger gripping portion of a tube with a series of slits, and then compressing the gripping portion to form a shoulder at a singular point of diameter change. While the reduced diameter grip of these applicators may help in preventing fingers from slipping towards the insertion end during the insertion step, there is little or no resistance offered in the opposite direction during the expulsion step. This is a step with which many users have difficulty.

To provide limited resistance to finger slippage during the expulsion step, annular ribs or circumferential ridges can be incorporated in the reduced diameter section, as disclosed in U.S. Pat. Nos. 4,921,474 and 3,831,605. However, in these examples, the projections extend to a lesser degree than a shoulder formed at the interface of the reduced diameter section and the remaining portion of the applicator insertion member. Forces required to expel materials from an applicator can be as great, or greater, than the forces required to place the insertion member into a body cavity, thereby necessitating the need for as great of resistance for the fingers in directions away from the insertion end as that towards the insertion end.

Another approach to improve the grip of the applicator during use is to incorporate projections, such as in the form of a ring, at the base of the applicator member being inserted into the body. Examples of this approach are disclosed in Voss, U.S. Pat. No. 4,361,150 and Sartinoranont, U.S. Pat. No. 4,447,222. In order for the projections to function as intended, they must be of significant dimension. However, a number of disadvantages are realized as the projection dimensions increase. One disadvantage is the handling of the applicators during high-speed manufacturing. Applicators are transferred from one position to another many times throughout its manufacture, and the projections can become snagged, severely affecting the output efficiency and quality of the products. Another feature of many high-speed manufacturing processes is a buffering system that accumulates materials and products between major steps of manipulation and assembly. Applicators with projections will not stack neatly (parallel) in the buffering systems, thereby negatively affecting the efficiency of space and transfer, and potentially creating a stop in the process due to applicators being "hung up" in the accumulators or interconnected with adjacent applicators.

A second disadvantage of applicators having projections is related to the packaging of the fully assembled applicators. Just as the applicators will not stack neatly in the buffering systems of high-speed manufacturing equipment, the applicators will not stack neatly in a package of two or more. Either extra packaging material is needed to compensate for non-parallel stacking, or additional equipment and processing steps is required to orient adjacent applicators such that the projections are opposite one another.

In view of the shortcomings of the prior art, what is needed is an applicator which has substantial resistance to finger slip during both applicator insertion into a body cavity and expulsion of material contained by the applicator, and is conducive to high-speed manufacturing and efficient packaging.

SUMMARY OF THE INVENTION

The present invention relates to methods of making applicators for delivering materials into body cavities. The applicators are particularly useful for inserting catemenial and prophylactic devices into a vaginal canal. The applicators comprise an elongate insertion member having an insertion end and a gripper end opposite thereof. The gripper end has an indentation with a shoulder on each end of the indentation. The shoulder disposed toward the insertion end provides resistance to finger slip during the step of inserting the applicator into a body cavity, while the shoulder adjacent the gripper end provides resistance to finger slip during the step of expelling material substantially contained by the applicator. The shoulder adjacent the gripper end also provides secure handling of the applicator while removing the applicator from the body after the expulsion step has been completed.

The indented finger grip feature provides additional benefits other than secure handling during use. The indentation provides a quick and easy visual/tactile cue of where to hold the applicator during use. A user's manual digits are somewhat protected from being significantly soiled with bodily-discharges. Furthermore, the indentation provides a visual/tactile cue of applicator insertion depth, and thereafter tampon positioning within the vaginal canal.

In accordance with one embodiment of the present invention there has now been provided a method of making an applicator for delivering materials into a mammalian body cavity, comprising an elongate insertion member having an indentation in a finger grip region defined by shoulders at each end of the indentation. The method includes providing an elongate insertion member having a gripper end. The gripper end has a first region proximal the gripper end edge, a second region adjacent the first region and distal the gripper end edge, and a third region adjacent the second region. Each region has an initial outside perimeter. The method also includes removing a plurality of discrete sections from the gripper end second region and reducing the outside perimeter of the second region while substantially maintaining the perimeter of the first and third regions. This forms an indented second region defined by a shoulder intermediate each of the first and second regions.

In accordance with a second embodiment of the present invention there has now been provided a method of making an applicator for inserting materials into a body cavity, comprising an elongate insertion member having an indentation in a finger grip region with shoulders on each end of the indentation. The method includes unwinding a rolled sheet-like material and separating the sheet-like material into a plurality of insertion member blanks. Each insertion member blanks has at least one gripper end, and the at least one gripper end has a first region proximal the gripper end, a second region adjacent the first region, and a third region adjacent the second region. The method also includes removing a plurality of discrete sections from the second region while maintaining portions of the material sections residing therebetween. The blank is formed around a mandrel and sealed to form an elongate formed member. The second region is then collapsed to form the indented second region defined by a shoulder intermediate the second region and each of the first and third regions.

Yet another embodiment provided by the present invention, similar to that above, employs the step of forming both the elongate insertion member and the indentation around the same mandrel, wherein the mandrel has a perimeter in a region corresponding to the blank second region which is less than a perimeter in regions corresponding to the blank first and third regions. This embodiment provides the potential for eliminating the need for a separate step to collapse the finger grip second region after the blank has been formed into an elongate member.

BRIEF DESCRIPTION OF THE DRAWING

FIGS. 2A–2D depict a sequence of steps (including optional steps) of a method for making tubular insertion members having an indentation in the finger gripping region, starting with a sheet of material.

DETAILED DESCRIPTION OF THE PREFERRED EMBODIMENT

Figure 1A:
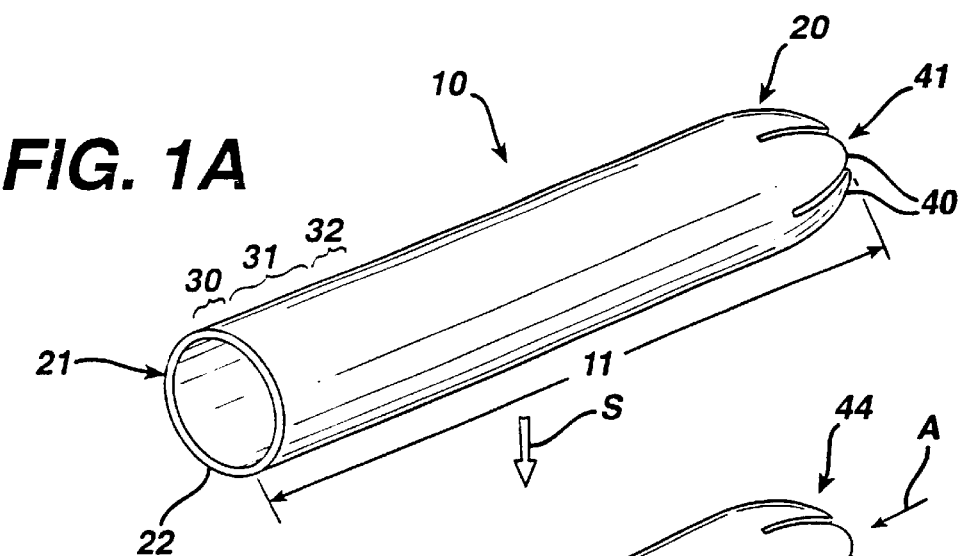
FIGS. 1A–1D depict a sequence of steps of a method for making tubular insertion members having an indentation in the finger gripping region, starting with a pre-made tubular structure.

The present invention relates to methods of making an applicator for delivering materials into mammalian body cavities. The applicator comprises an elongate insertion member that is intended to be at least partially inserted into a body cavity. The elongate insertion member has a length that extends from an insertion end to a gripper end. To improve a user's ability to securely hold the applicator during use, the gripper end of the insertion member incorporates an indentation defined by shoulders at each end thereof.

Referring now to the drawings, wherein like reference numerals designate like elements. Arrows labeled with "S" illustrate possible sequencing of the steps as described in the methods herebelow.

Figure 1B:
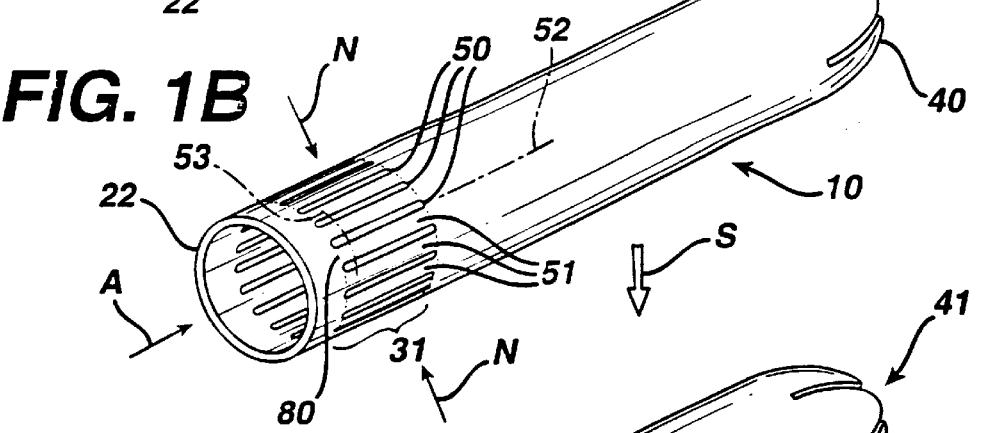
Figure 1C:
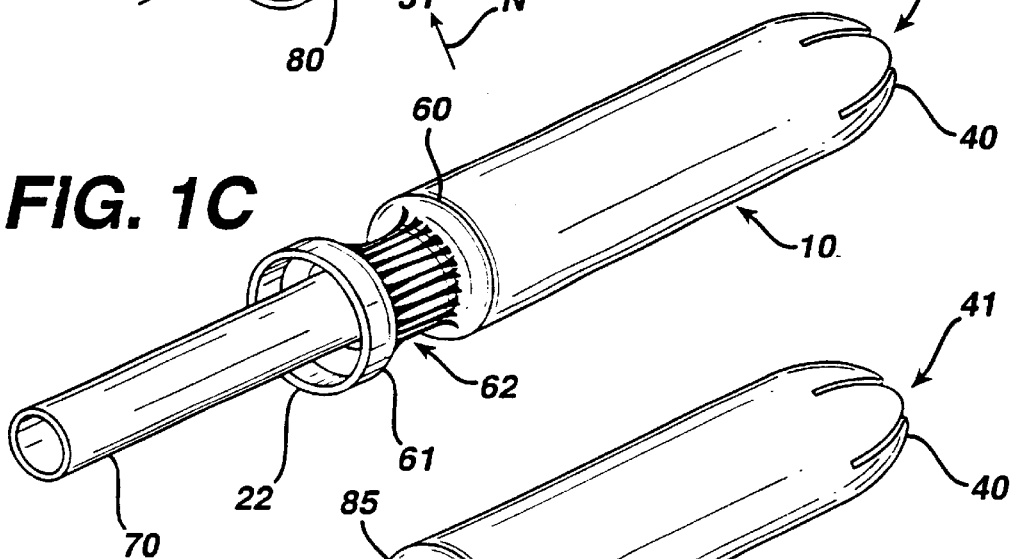

The applicator of the present invention can be made by manipulating a pre-made insertion member through a series of steps as can be seen in FIGS. 1A–1C. FIG. 1A depicts a pre-made, elongate, tubular insertion member 10, having a length 11, an insertion end 20 and a gripper end 21 opposite thereof, and optionally a plurality of inwardly curved petals 40 to form a substantially closed dome 41. The gripper end 21 comprises a gripper edge 22 and three adjacent regions: first region 30, second region 31, and third region 32. The second region 31 should be of sufficient length to accept an ordinary person's finger or thumb. First region 30 and third region 32 are preferably much shorter in length compared to the second region 31. The tubular insertion member 10 may be made by any number of techniques known to one having ordinary skill in the art, such as by injection molding, blow molding, extruding, spiral winding, forming around a mandrel, and the like.

A plurality of discrete sections 50 are removed from the second region 31, while maintaining non-removed sections 51, as shown in FIG. 1B. A representative, non-limiting list of methods useful for removing the sections 50 is the following: die-cutting, laser cutting, water jet cutting, thermoforming, grinding, and the like. The removed sections 50 have a major axis 52 and a minor axis 53, with the major axis 52 preferably oriented substantially parallel to the length 11 of the tubular insertion member 10. Alternatively, the major axis 52 may be oriented at an angle, less than 90°, to the length 11 of the tubular insertion member 10. The removed sections 50 have a length dimension that is parallel to the major axis 52 from about 40 to about 90 millimeters, and a width dimension that is parallel to the minor axis 53 from about 0.2 to about 1.5 millimeters. The length dimensions may be constant or varying along the periphery of the removed sections 50.

Referring to FIG. 1C, after removing the discrete sections 50, the second region 31 is collapsed to form an indentation 62 defined by shoulders 60 and 61 intermediate the second region 31 and each of the first region 30 and third region 32, respectively. These shoulders 60 and 61 collectively provide resistance to finger/thumb slip in two directions. Applying a normal force N to the second region 31, or applying a combined axial force A to the tubular insertion member 10 and a normal force N to the second region 31, the second region 31 can be collapsed, as shown in FIG. 1B. The collapsed second region 31 then has a perimeter that is less than the perimeter of the first region 30 and third region 32. As used herein in the specification and claims, the term "perimeter" relates to the measurement about the structure as measured in and defined by a plane perpendicular to the longitudinal axis of the blank or the insertion member. This measurement may be on the inside or the outside of the structure. The perimeter of a substantially tubular structure is related to its diameter.

The collective amount of material removed in the second region 31 will generally dictate the difference in diameter of a tubular member between the collapsed second region 31 and the first and third regions 30 and 32. Preferably, the diameter of the collapsed second region 31 is no greater than about 90% of the diameter of the first and third regions 30 and 32, and more preferably no greater than about 70%. If this is measured as a perimeter, the collapsed perimeter is preferably no greater than about 90% of the perimeter of the first and third regions 30 and 32, and more preferably no greater than about 70%.

A further step of weakening the non-removed sections 51 in the second region 31 can optionally be employed prior to collapsing the second region. Two benefits derived from this optional weakening step are a decreased amount of force required to collapse the second region 31, and improved aesthetics of the non-removed sections 51, yielding a substantially smooth, wrinkle free surface. Representative, non-limiting techniques useful for weakening the non-removed sections 51 includes providing one or more scored or perforated lines, skiving, providing one or more embossed areas, an the like. Preferably scored or perforated lines 80 are incorporated in the transverse direction of the non-removed sections 51 at the interface between the second region 31 and each of the first region 30 and third region 32, as can be seen in FIG. 1B.

Referring again to FIG. 1C, when a user inserts the tubular insertion member 10 into a body cavity, her fingers and/or thumb are urged towards the insertion end 20 due to the frictional forces between the insertion member 10 and the walls of a body cavity. Shoulder 61 provides resistance to this movement, thereby providing a secure hold during insertion. Once the tubular insertion member 10 is successfully inserted into the body, a user can expel material contained by the applicator. This is typically performed by displacing an elongate expulsion member, shown as element 70, into the tubular insertion member 10. During the expulsion step, her fingers and/or thumb are urged in the opposite direction, towards the gripper edge 22 due to a potential combination of many factors. These factors include frictional forces between insertable material (not shown) and the inner wall of the tubular insertion member 10, and the forces required to open the substantially closed dome 41. Shoulder 60 provides resistance to this particular movement, thus providing a secure hold during the expulsion step of use.

Alternatively, the present invention provides methods of making applicators having an indentation in the finger grip region starting with sheet-like material. Referring now to FIGS. 2A–2C, a roll of sheet-like material 100 is unwound and separated into a plurality of insertion member blanks 101. The blanks 101 have at least one gripper end 103 defined along a longitudinal axis 104. The gripper end 103 comprises a first region 110 proximal a gripper end edge 105, a second region 111 adjacent the first region 110, and a third region 112 adjacent the second region 111. Next, a plurality of discrete sections 120 are removed from the second region 111, while maintaining non-removed sections 121 residing between the removed sections 120. It is also possible for the discrete sections 120 to be removed simultaneously with the step of separating the roll 100 into the plurality of insertion member blanks 101. This alternative method can be accomplished by employing a multi-component die or by a combination of dies and/or knives.

The insertion member blanks 101 are then transferred to and formed around a structure, such as a mandrel 130, to form an elongate formed member, for example a substantially tubular member 131 having a sealed seam 132. The elongate member may form a single insertion member 131, or it may have a gripper end at each end of the elongate formed member. The elongate formed member may then be separated to form two individual insertion member 131 as described in Hinzmann, U.S. Pat. No. 4,755,164.

One embodiment provided by the present invention includes removing the tubular member 131 from the mandrel 130, and then collapsing the second region 111 to a diameter less than a diameter of the first region 110 and third region 112. Any number of apparatus and methods can be employed to apply sufficient force to collapse the second region 112, such as by use of a two hemispherical collars applying pressure from a pneumatic cylinder, or by rotating the tubular member 131 and contacting the second region 112 with an axially displaced probe, or the like.

Figure 3:
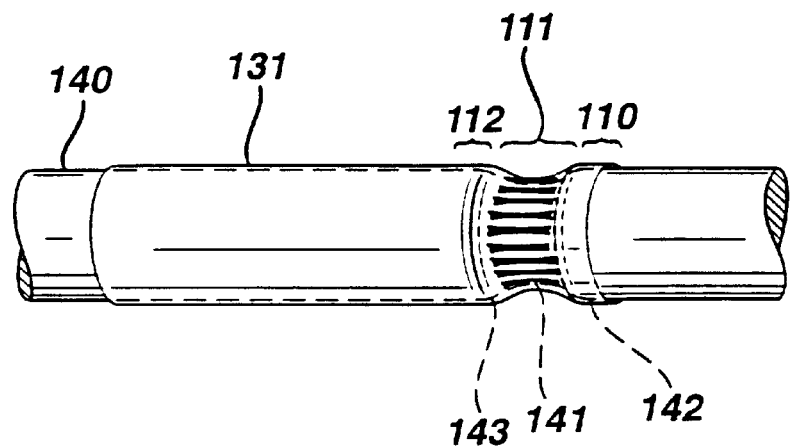
FIG. 3 depicts an alternative sequence to that in FIGS. 2C–2D.

As shown in FIG. 3, an alternative embodiment includes the step of forming the tubular member 131 and collapsing second region 111 simultaneously, such as by the use of a mandrel 140 having a diameter in a region 141 corresponding to the second region 111, which is less than a diameter in regions 142 and 143 corresponding to the first region 110 and third region 112 respectively.

Similar to starting with a pre-made tubular insertion member, a further step of weakening the non-removed sections 121 can be employed when making applicators from sheet-like material.

Figure 1D:
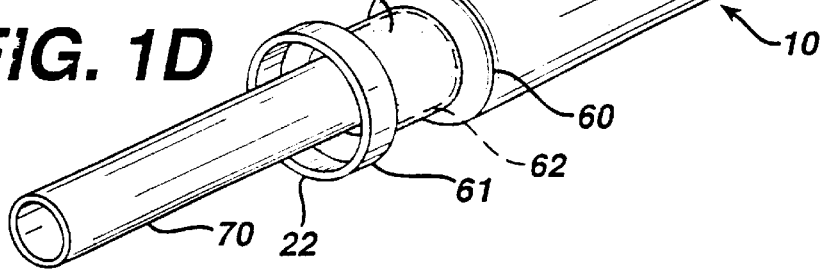

Several techniques can be employed to help maintain the indentation 62 once it is formed. These techniques generally comprise incorporating additional materials and/or elements within at least portions of the indentation 62, prior to, or after, its formation. One technique is to overlay the collapsed second region 31 with an elastomeric element, such as in the form of a ring (shown as element 85 in FIG. 1D). The elastomeric element 85 has an inside perimeter substantially equivalent to the collapsed perimeter of the second region 31 when its in a substantially relaxed condition. The elastomeric element 85 is capable of elongating (elastic deformation in the absence of plastic deformation) under an applied load, sufficiently to fit over the non-collapsed perimeter of the first region 30 and third region 32 that are adjacent the collapsed second region 31. Once the load is removed or the elastomeric element is relaxed, the elastomeric element substantially resumes it original dimensions, thereby maintaining the gripper end indentation 62. Materials useful for the constructing the elastomeric element include, but are not limited to, natural rubber, neoprene rubber, butyl rubber, styrene rubber, nitrile rubber, metallocene such as EXXACT brand polymers from Exxon, polysiloxanes, and the like. An additional benefit to many of the above materials is their frictional properties, which provides further resistance to finger/thumb slip during use of the applicator.

A second technique for maintaining the gripper end indentation 62 once it is formed, is overlaying the second region 31 with a shrinkable polymeric material, such as low density polyethylene, and then applying energy, such as by heated air at temperatures from about 160° C. to about 180° C., to the second region 31 in an amount sufficient to induce shrinking of the shrinkable polymeric material. The shrinkable polymeric material will have an initial inside perimeter, and upon being heated will have a reduced inside perimeter substantially equivalent to the final outside perimeter of the second region.

Figure 4:
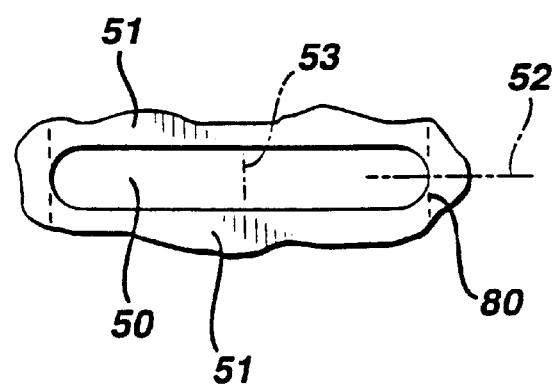
FIG. 4 is an enlarged view of the gripping region taken from FIG. 1B.
Figure 5:
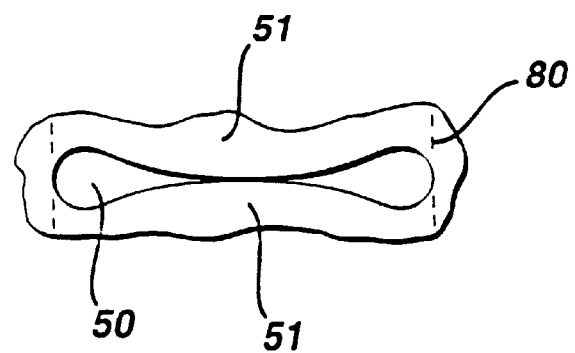
FIG. 5 is an enlarged view of the gripping region taken from FIG. 1C.

FIGS. 4 and 5 illustrate enlarged sections of the gripper end 21 taken from FIGS. 1B and 1C, respectively. In the maximum collapsed state, at least central edges 90 of adjacent non-removed sections 51 are abut. FIGS. 4 and 5 are particularly useful for illustrating additional, alternative techniques for maintaining the gripper end indentation 62 discussed herein below.

Another method of maintaining the gripper end indentation is to apply an adhesive to portions of the non-removed sections 51 where they abut. The adhesive in a cured condition will hold the non-removed sections 51 together.

The gripper end second region 31 may optionally comprise thermoplastic material. Energy may be applied to the thermoplastic material in an amount sufficient to induce flow of the thermoplastic material. Available thermoplastic material bridging the abut non-removed sections 51 will hold the non-removed sections together after the energy is removed, thereby maintaining the final outside perimeter of the second region.

Where the applicator is constructed mainly from a thermoplastic material, such as a polyolefin, energy and pressure can be employed to reposition the second region 31 to an equivalent collapsed state, and upon removal of the energy and pressure, the second region will remain repositioned. This can be accomplished by any number of techniques known in the art, including the use of heated air, wherein the source of the heated pressurized air does not contact the second region, thereby eliminating any issues of the tubular insertion member sticking to the source, which could result in quality and maintenance issues. An alternative technique consists of vacuum forming.

The applicators of the present invention can be made of materials generally known to those of ordinary skill in the art, such as plastics (polymers) and cardboard. The plastic applicators may be of conventional polymers, such as polyolefins, or be of more sophisticated polymers and polymer blends formulated to provide features such as biodegradability and/or water dispersibility. Examples of applicators that are designed to be dispersible or biodegradable are disclosed in the following U.S. Pat. Nos. 5,002,526 and 5,782,794 relating to applicators made from polyvinyl alcohol based compositions, U.S. Pat.No. 5,350,354 relating to applicators made from starch based compositions, and U.S.Pat. No. 4,900,299 relating to applicators made from poly(3-hydroxybutyric acid) based compositions. Plastic applicators are typically made by the following non-limiting processes: injection-molding, blow-molding, and extrusion.

Cardboard applicators can be constructed from a single layer of cardboard material, or from a plurality of laminated layers to provide multiple benefits relating to the various layers. Useful cardboard stock for the formation of the tubular insertion members and expulsion members include, without limitation, paperboard, cardboard, cup stock, paper, and the like. The applicators can be made by the following non-limiting processes: spiral winding as disclosed in U.S. Pat. No. 5,346,468, convolute winding as disclosed in U.S. Pat. No. 4,508,531, and forming a sheet around a mandrel and then sealing an overlapped seam as disclosed in U.S. Pat. No. 4,755,164.

The cardboard applicators may include a surface layer, which may be useful to increase the comfort and ease of insertion and withdrawal of the applicator. The surface layer may be in the form of laminated films, cured coatings, and the like. An example of such a surface layer is disclosed in Blanchard, co-pending application U.S. Ser. No. 09/105,787 filed on Jun. 26, 1998. A representative, non-limiting list of useful materials to be used as the surface layer includes, waxes, cellophane, polyolefins, polyesters, epoxies, and the like. The surface layers may also include thermal stabilizers, pigments, fragrances, surfactants, antimicrobial agents, medicaments, and the like. There are many techniques known for applying the surface layers. A representative, non-limiting list of such techniques includes spraying, extruding, slot-coating, brushing, transfer coating, and the like. Additional processing steps may be required to cure the surface treatments to a useable form other than simple air curing, such as applying irradiation or other forms of energy.

Typical dimensions for each of the tubular insertion and expulsion members include a length of from about 50 to about 100 millimeters, a diameter of from about 8 to about 16 millimeters, and a thickness of from about 0.4 to about 0.6 millimeters. Preferably, the diameter of the expulsion member 70 is less than the diameter of the tubular insertion member 10 to allow for a telescopic arrangement of the two, as shown in FIG. 1.

The insertion end of the applicator can be more or less open, that is the perimeter along the length of the insertion member is substantially equivalent to the perimeter of the insertion end. Procter & Gamble, of Cincinnati, Ohio, currently offers for sale an open-ended, tubular tampon applicator under the trade name TAMPAX brand flushable applicator tampons.

However, it is preferred that the elongate insertion member of the applicator provided by the present invention be substantially closed prior to expulsion of the materials contained therein. One technique for substantially closing the insertion end 20 of the tubular insertion member 10 employing a plurality of inwardly curved petals 40 is shown in FIG. 1. The petals will flex and/or hinge to an open position upon expelling materials contained by the applicator. The number of petals generally ranges from about 4 to about 6.

An alternative technique for substantially closing the insertion end of an applicator is by pleating the insertion end. This technique is disclosed in U.S. Pat. No. 5,782,793. When an applicator is constructed with more than one layer of material, a single layer may extend into the insertion end in an effort to reduce the force required to expel the contained materials. An example of this is disclosed in U.S. Pat. No. 5,827,214. The enclosed insertion end may be of any number of shapes including spherical and tapered.

Preferably the applicators provided by the present invention are cylindrical tubes that are substantially straight along their lengths, not including their gripper end. The applicators may however, be curvilinear to improve comfort and manipulation of the applicator during insertion and withdrawal from a body cavity. An example of a curved applicator can be seen in U.S. Pat. No. 5,158,535.

The applicator of the present invention can be used for the delivery of catamenial devices, such as tampons, intravaginal collection devices, and interlabial pads. The applicator may also be useful for delivery of oral, rectal, and vaginal suppositories, as well as nasal devices, such as nasal tampons. Further, the applicator can be used for delivery of various other materials including, medicaments, moisturizers, vitamins and minerals, spermicides, and odor controlling agents. These materials may be in the form of solids, creams, foams, gels, and the like.

The disclosures of all US patents and patent applications, as well as any corresponding published foreign patent applications, mentioned throughout this patent application are hereby incorporated by reference herein.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of making an applicator for delivering materials into a mammalian body cavity, the applicator comprising an elongate insertion member having an indentation in a finger grip region with shoulders on each end of the indentation, comprising the steps of:

a) unwinding a rolled sheet-like material;

b) separating the sheet-like material into a plurality of insertion member blanks, having a longitudinal axis and at least one gripper end, the at least one gripper end having a first region proximal a gripper end edge, a second region adjacent the first region and distal the gripper end edge, and a third region adjacent the second region;

c) removing a plurality of discrete sections from the second region while maintaining portions of the material sections residing therebetween;

d) forming the blank around a forming mandrel that is oriented parallel to the longitudinal axis of the blank;

e) sealing a longitudinal seam defined by the formed blank to form an elongate formed member having a longitudinal axis parallel to the longitudinal axis of the blank; and f) collapsing the second region to a perimeter less than a perimeter of the first and third regions, each perimeter defined by a plane perpendicular to the longitudinal axis of the elongate formed member thereby forming a gripper end having an indentation defined by a shoulder intermediate the second region and each of the first and third regions.

2. The method of claim 1 further comprising the step of overlaying the second region with an elastomeric element having an inside perimeter defined by a plane perpendicular to the length of the insertion member that is substantially equivalent to the final outside perimeter of the second region when measured in a substantially relaxed condition.

3. The method of claim 1 further comprising the steps of overlaying the second region with a shrinkable polymeric material having an initial inside perimeter defined by a plane perpendicular to the longitudinal axis of the insertion member, and applying sufficient energy to reduce the inside perimeter of the polymeric material to a dimension substantially equivalent to the final outside perimeter of the second region.

4. The method of claim 1 further comprising the steps of applying adhesive to at least a portion of the non-removed sections to adhere adjacent non-removed sections, to maintain the final outside perimeter of the second region.

5. The method of claim 1 further comprising the step of weakening the non-removed sections.

6. The method of claim 1 wherein the insertion member blank has two gripper ends, and wherein the method further comprises the step of separating the elongate formed member in a plane perpendicular to its longitudinal axis to form two insertion members, each having a gripper end and an opposed insertion end.

7. The method of claim 1 wherein the insertion member blank has one gripper end and an opposed insertion end.

* * * * *